(12) United States Patent
Adriansens (10) Patent No.: US 8,083,512 B2
(45) Date of Patent: Dec. 27, 2011

(54) FURNACE AND EQUIPMENT FOR PRODUCING STERILE VESSELS FROM DECONTAMINATED PREFORMS OF A THERMOPLASTIC MATERIAL

(75) Inventor: Eric Adriansens, Octeville sur Mer (FR)

(73) Assignee: Sidel Participations, Octeville-sur-Mer (FR)

( * ) Notice: Subject to any disclaimer, the term of this patent is extended or adjusted under 35 U.S.C. 154(b) by 459 days.

(21) Appl. No.: 12/447,418

(22) PCT Filed: Oct. 25, 2007

(86) PCT No.: PCT/EP2007/061458
§ 371 (c)(1),
(2), (4) Date: Apr. 27, 2009

(87) PCT Pub. No.: WO2008/049876
PCT Pub. Date: May 2, 2008

(65) Prior Publication Data
US 2009/0317506 A1    Dec. 24, 2009

(30) Foreign Application Priority Data
Oct. 26, 2006    (FR) ...................................... 06 54545

(51) Int. Cl.
*B29C 49/68*    (2006.01)
(52) U.S. Cl. ...................... 425/174.4; 422/303; 422/304; 425/526
(58) Field of Classification Search ............... 425/174.4, 425/526; 422/303, 304
See application file for complete search history.

(56) References Cited

U.S. PATENT DOCUMENTS

| | | | |
|---|---|---|---|
| 3,911,640 A | 10/1975 | Rausing | |
| 4,313,720 A * | 2/1982 | Spurr | 425/526 |
| 5,322,651 A | 6/1994 | Emmer | |
| 5,618,489 A * | 4/1997 | Weissmann | 264/530 |
| 6,183,691 B1 | 2/2001 | Swank et al. | |
| 6,361,301 B1 * | 3/2002 | Scaglotti et al. | 425/174.4 |
| 6,517,776 B1 | 2/2003 | Rodgers et al. | |
| 6,562,281 B1 * | 5/2003 | Marchau et al. | 264/532 |
| 7,806,680 B2 * | 10/2010 | Adriansens et al. | 425/526 |
| 7,938,639 B2 * | 5/2011 | Adriansens et al. | 425/210 |
| 2010/0047120 A1 * | 2/2010 | Adriansens et al. | 422/22 |
| 2011/0133370 A1 * | 6/2011 | Engelhard et al. | 264/535 |

FOREIGN PATENT DOCUMENTS
EP    0411970    2/1991
(Continued)

OTHER PUBLICATIONS
International Search Report dated Jan. 23, 2008, in PCT application.

*Primary Examiner* — Robert B Davis
(74) *Attorney, Agent, or Firm* — Young & Thompson (57) ABSTRACT

The invention relates to a thermal conditioning furnace (10) including a first infrared (IR1) heating element (32), an ultraviolet (UV) sterilizer (76) and a second infrared (IR2) heating element (34) for successively carrying out a decontamination for sterilizing at least the outer surface (28) of the body (14) of the perform (12), and to an equipment (56) including such a furnace (10) for producing sterile vessels (68) by a blowing or stretching-blowing technique from decontaminated performs (12) of a thermoplastic material.

12 Claims, 3 Drawing Sheets

FOREIGN PATENT DOCUMENTS

| | | |
|---|---|---|
| EP | 0564354 | 10/1993 |
| EP | 0620099 | 10/1994 |
| FR | 2195551 | 3/1974 |
| FR | 2464816 | 3/1981 |
| FR | 2872734 | 1/2006 |
| WO | 9903667 | 1/1999 |
| WO | 9951497 | 10/1999 |
| WO | 2006010694 | 2/2006 |

* cited by examiner

FURNACE AND EQUIPMENT FOR PRODUCING STERILE VESSELS FROM DECONTAMINATED PREFORMS OF A THERMOPLASTIC MATERIAL

The invention relates to an oven and to an installation for the manufacture of sterile receptacles starting from decontaminated thermoplastic preforms.

The present invention relates generally to the sector of sterilization (or decontamination) of thermoplastic preforms, particularly those made from polyethylene terephthalate (PET), which are intended for the manufacture of receptacles, such as bottles, vials or the like, by a process of blow molding or stretch blow molding of a preform previously heat-conditioned in an oven.

One of the aspects of the invention relates to an oven for heat-conditioning of thermoplastic preforms intended for the manufacture of hollow-bodied receptacles by blow molding or stretch blow molding, comprising a device for transport of the preforms which are rotated around their own axes and successively conveyed within at least:
- one first zone, which may be called a deep-heating zone, comprising first means for heating by infrared radiation intended to preheat the body of each preform up to a first setpoint temperature;
- a second zone, which is an intermediate zone, and which may be called a residence zone, through which zone, which is interposed in the path of the preforms between the first zone, which is a heating zone, and a third zone, which is a heating zone, each preform panes, during a defined period;
- the third zone, which may be called a distributed-heating zone, comprising second means for heating by infrared radiation, intended to heat the body of each preform, in accordance with a defined heater profile, up to a second setpoint temperature.

There are many known ovens of this type in particular for the heating of a preform by infrared radiation in order to heat-condition the same with the aim of molding the same, i.e. of converting it by blow molding into a receptacle, such as a bottle, and this type of oven is then integrated into an installation for manufacture of which it constitutes one of the principal units.

Documents EP-A-0,620,099 or EP-A-0,564,354 respectively describe examples of an oven for heat-conditioning of the body of a preform intended for the manufacture of a receptacle.

It is known that preforms intended for the manufacture of sterile or decontaminated receptacles in an installation are advantageously treated at the start of the process of manufacture of the receptacles, rather than at the end of the process of manufacture after the receptacle has been obtained by blow molding, because this reduces the amount used of the sterilizing product, this amount being partly a function of the surface area to be decontaminated.

Another aspect of the invention relates to an installation for the manufacture of sterile receptacles, starting from a decontaminated thermoplastic preform, which generally comprises at least:
- one device for feed of preforms;
- one unit for heat-conditioning comprising a device for transport of preforms which are rotated around their own axes and conveyed through at least one oven intended to heat each preform with the aim of molding of the same; and
- a unit for molding comprising at least one mold and an associated device for blowing intended to convert each preform to a hollow-bodied receptacle.

There are many known installations for the manufacture of sterile receptacles of this type by blow molding or stretch blow molding, additionally comprising means for sterilization of these preforms, for example by a chemical method, particularly by wetting the surfaces to be decontaminated by soaking in a sterilizing solution, such as a solution of hydrogen peroxide ($H_2O_2$).

Document WO-A-99/03667 describes, for example, a process for the manufacture of sterile receptacles and an installation for operating this process.

The installation shown in FIG. 5 of that document comprises principally a device for feed of preforms, a unit for heat-conditioning comprising a device for transport of preforms through at least one oven intended to heat each preform with the aim of molding of the same, and a unit for molding comprising at least one mold and an associated device for blowing intended to convert each preform into a final hollow-bodied receptacle.

In that installation, the preforms are treated by means for sterilization, upstream of the oven for heating of the preform, in such a way as to decontaminate the cylindrical surface of the internal wall of the preform.

The internal wall of the preform corresponds to the internal wall of the hollow-bodied receptacle intended to be manufactured by blow molding starting from said preform, and said internal wall of the preform therefore delimits the interior volume of the receptacle intended for final filling, for example with a given liquid in the case of a bottle or a vial.

The means for sterilization described in that document comprise particularly a sterilization product such as a solution of hydrogen peroxide ($H_2O_2$), which is activated thermally by the heat from the means for heating of the oven, prior to being removed by evaporation.

To this end, the means for sterilization comprise a sprayer constituted by a spray gun permitting wetting of the interior of the preforms with "cold" sterilization product, i.e. one which has not been previously heated and is therefore in the liquid state.

The gun is typically a bifluid gun comprising a nozzle for liquid and a nozzle for air forming a circular projection assembly which can be placed above the path of the preforms in such a way as to spray a mist of sterilization product.

The mist of sterilization product is formed from a cloud of droplets which is projected by the gun in the direction of the interior of the preform in turbulent flow.

It has been found that this type of turbulent flow of sterilization product inside the preform leads to non-homogeneous distribution of droplets on the internal wall of the preform.

The reason for this is that the use of a spray gun is characterized in particular by a high flow rate of sterilizing product, this being obtained by compression of a gas, such as air compressed to pressures of from about 2 to 3 bar, thus producing turbulent flow.

Now, turbulent flow leads to non-homogeneous deposition of residual droplets of sterilizing product on the internal walls of the preforms. Furthermore, the droplets of sterilizing product form an excess which is not entirely vaporized during heating.

These droplets of sterilizing product therefore firstly cause local chemical attack on the material of the preform, generally made from polyethylene terephthalate (PET) and secondly, during the heating of the preforms, produce a magnifying-glass effect on the thermal radiation used in the heating process, and this causes spots to appear on the walls of the receptacles, for example bottles, resulting from the treated preforms.

The appearance of these spots on the walls of the bottles is a visual defect on the product which is also sometimes termed "orange-peel appearance".

Furthermore, the amount of sterilization solution that can be used is limited by legal obligations to remove the sterilization solution, the absolute maximum acceptable residual being very minute traces of the solution on the sterilized receptacle, with the particular objective that the amount of sterilization solution found in the liquid intended to fill the receptacle is not above the legal limit.

Receptacles manufactured by that process are consequently not entirely satisfactory and moreover are not found to have an adequate degree of decontamination in relation to the level of sterility required for certain industrial applications.

The reason for this is that the decontamination process operated in the installation according to that process relates only to the internal wall of the preform. However, the external surface of the body of the preform analogously comprises microorganisms, bacteria, or spores which can contaminate the preforms (or the receptacles) as well as the general manufacturing installation.

Now, the microorganisms, bacteria, etc. present on the external surface of the body of the preform can propagate in the installation, particularly by using, as carrier, the flow of cooling air passing around the preforms in the oven, or else by contaminating the surface of the molds of the blowing unit of the installation.

There is consequently a risk of contamination, also sometimes termed "risk of cross-contamination", insofar as the presence of microorganisms, etc. on the external surface of the preform can given rise to contamination capable of affecting the sterility of the final receptacle or of entire batches or receptacles, particularly the internal sterility.

That is one of the reasons for searching for solutions which permit very particularly effective decontamination of the external surface of the body of each preform.

One possible solution consists in treating the external surface of the body of the preform by a chemical method in a manner analogous to that for the internal wall, i.e. by spraying a sterilization solution, such as a solution of hydrogen peroxide ($H_2O_2$), on the external surface of the body of the preform, upstream of the oven for heat-conditioning.

However, trials demonstrated that the flow of cooling air passing through the oven causes almost systematic and immediate removal of most of the sterilization solution applied on the external surface, and that this occurs before the sterilizing solution can be thermally activated by the means of heating, the result being that the decontamination thus obtained on the external surface of the body of the preform is generally of a very low level and therefore inadequate for achieving a high final degree of decontamination.

The invention is aimed at removing these disadvantages by proposing a novel oven which in particular permits manufacture of these sterile receptacles in a simple, reliable and cost-effective manner, in accordance with a global process of sterilization of a preform, in one installation for manufacture of sterile receptacles by blow molding or by stretch blow molding of preforms, starting from preforms which have been entirely sterilized or decontaminated, not only in the interior but also on the exterior.

The invention is very particularly, but not exclusively, aimed at the sterilization of the external surface of the body of a preform, i.e. at the reduction of the level of contamination of that surface by microorganisms, bacteria, or spores, etc., with the very particular aim of limiting the risk of cross-contamination.

To this end, the invention proposes an oven for heat-conditioning of thermo-plastic preforms, particularly intended for equipping an installation for manufacture of sterile receptacles by blow molding or stretch blow molding, comprising a device for transport of the preforms which are rotated around their own axes and successively conveyed within at least:
  one first zone, which may be called a deep-heating zone, comprising first means for heating by infrared radiation intended to preheat the body of each preform up to a first setpoint temperature;
  a second zone, which is an intermediate zone, and which may be called a residence zone, through which zone, which is interposed in the path of the preforms between the first zone, which is a heating zone, and a third zone, which is a heating zone, each preform passes during a defined period;
  the third zone, which may be called a distributed-heating zone, comprising second means for heating by infrared radiation, intended to heat the body of each preform, in accordance with a defined heater profile, up to a second setpoint temperature,
characterized in that the oven comprises means for sterilization by emission of ultraviolet (UV) radiation, arranged in the second zone, which is an intermediate residence zone, in such a way as to sterilize at least the external surface of the body of the preform up to a defined degree of decontamination.

According to other characteristics of the oven according to the invention:
  the oven comprises means for reflection, such as reflectors, arranged in the second zone, which is an intermediate residence zone, opposite to the means for sterilization by ultraviolet radiation, such as lamps, in such a way as to reflect selectively the ultraviolet radiation emitted in the direction of the preforms passing between the means for sterilization and the means for reflection;
  the oven comprises a device for the cooling of the preforms by passage of a current of air around the preforms, characterized in that the ultraviolet radiation emitted by the means for sterilization in the second zone, which is an intermediate residence zone, sterilizes the air circulating around the preforms;
  the device for transport comprises means for grasping the neck of each preform comprising at least one internal core which penetrates axially into the interior of the neck of the preform in such a way that the ultraviolet radiation emitted by the means for sterilization irradiates entirely the neck of the preform.

The invention also proposes an installation of the type described above for the manufacture of sterile receptacles starting from a decontaminated thermoplastic preform, following the sterilization process, characterized in that the installation comprises an oven for heat-conditioning comprising:
  first means for heating intended to decontaminate at least the external surface of the body of the preform by pre-heating the body of each preform up to a first setpoint temperature;
  means for sterilization by emission of ultraviolet radiation intended to decontaminate at least the external surface of the body of the preform by irradiation of the preform (12) exposed during a defined period ($\Delta t$) to ultraviolet (UV) radiation emitted by the means for sterilization (76); and second means for heating intended to decontaminate at least the external surface of the body of the preform by heating the body of each preform up to a second setpoint temperature, in such a way as to sterilize at least the external surface of the body of the preform up to a defined degree of decontamination.

The installation advantageously comprises, upstream of the oven for heat-conditioning, a unit for sterilization comprising a device for projection of sterilizing product provided with at least one nozzle capable of projecting, in the form of a vapor jet, a flow of sterilizing product toward the aperture of the neck of each preform, the temperature of which is lower than the temperature of condensation of the sterilizing product, in such a way as to deposit by condensation on at least the internal wall of the preform an approximately uniform condensation film of sterilizing product, intended to sterilize at least the internal wall.

The first temperature of preheating and/or the second temperature of heating of the body of the preform are advantageously higher than or equal to the temperature of activation of the sterilizing product, in such a way that the sterilizing product is activated by heating in order to sterilize the internal wall of the preform.

It is advantageous that the first temperature of preheating and/or the second temperature of heating of the body of the preform are higher than the temperature of evaporation of the sterilizing product, in such a way as to remove by evaporation the sterilizing product activated by heating.

In general terms, it will be remembered that within the sector at which the invention is aimed, the level of sterility of a preform or of a receptacle is appraised as a function of the number of microorganisms, bacteria, or spores, and the phrase most often used is therefore the degree of decontamination obtained.

The level of sterility or degree of decontamination is determined by counting the number of microorganisms, etc., these being enumerated after washing, filtration and culturing, the number generally being expressed as "log", depending on the logarithmic reduction in the number of microorganisms, etc.

By way of example, when the degree of decontamination corresponds to a reduction of 1000 units ($10^3$), the logarithmic reduction of the number of microorganisms is said to amount to 3 log, or else 3D.

The level of sterility is of course determined as a function of the applications, and the degree obtained being proportional to the logarithmic reduction in the number of microorganisms, etc., a degree of decontamination amounting to 1 log is mostly considered to be slight or negligible, while a degree of decontamination amounting to 6 log is mostly considered to be extremely high.

Other characteristics and advantages of the invention will be apparent from reading the detailed description that follows, the understanding of which will be assisted by using the attached drawings, in which.

In the description, non-limiting interpretations apply to expressions such as "upstream" and "downstream", "higher" and "lower", and "interior" and "exterior", and the longitudinal, vertical and transversal orientations with reference to trihedral systems (L, V, T) shown in the figures and in definitions given in the description.

The same reference symbols will be used for similar or identical elements throughout the remainder of the description.

Figure 1:
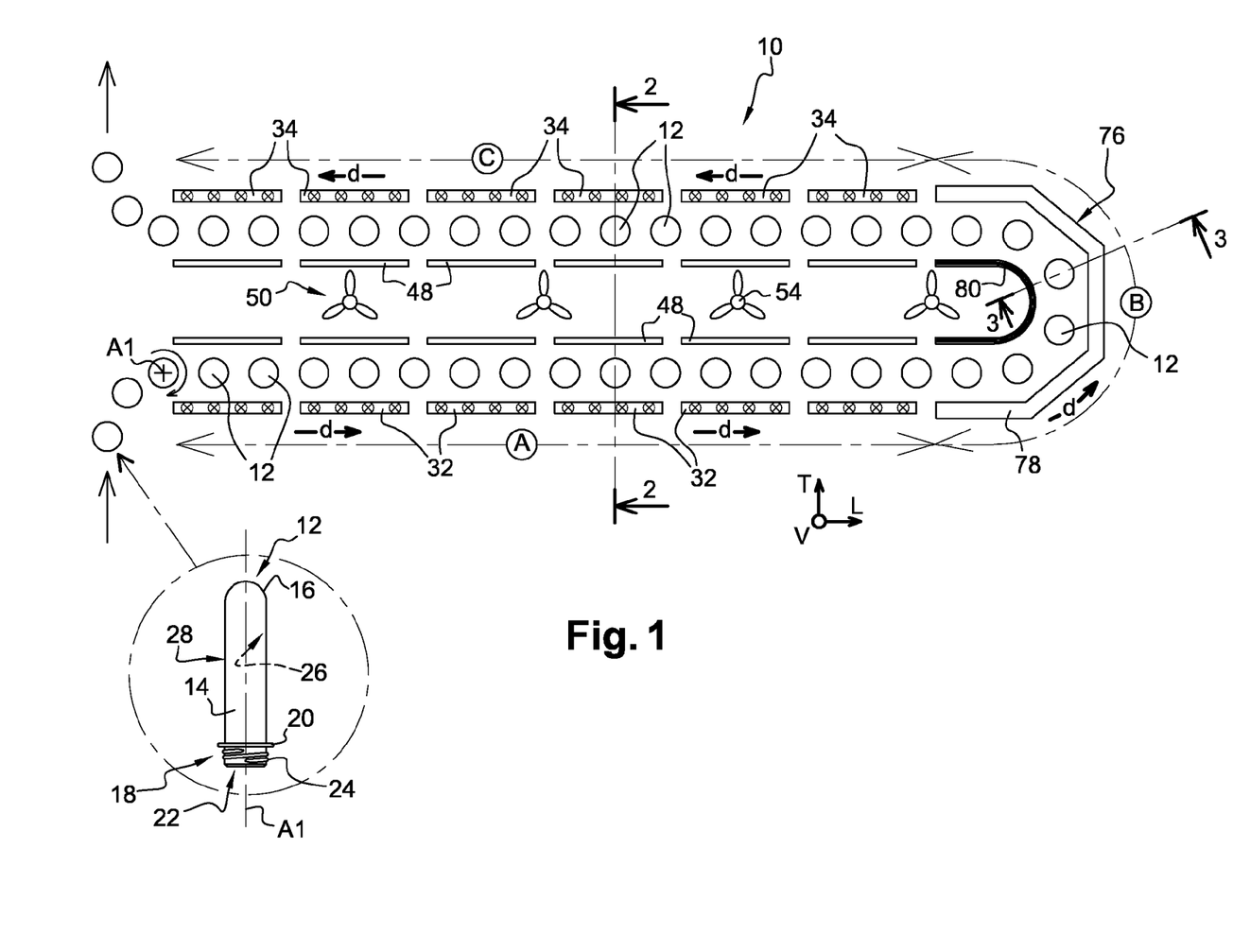
FIG. 1 is a diagrammatic plan view of an oven for heat-conditioning according to the invention.

FIG. 1 shows an embodiment of an oven 10 for heat-conditioning preforms, in particular plastic or thermoplastic preforms, for example polyethylene terephthalate (PET) preforms.

FIG. 1 shows a detailed view of a preform 12 intended for the manufacture of a hollow-bodied receptacle, for example a bottle, a vial, etc., particularly by blow molding or by stretch blow molding.

The term "preform" is defined as designating in the remainder of the present description either the preform initially obtained by injection of plastic and used in processes of manufacture of a receptacle having a single blow molding step leading directly to the final receptacle or the intermediate receptacle in the case of processes having a plurality of blow molding steps.

The preforms 12 are generally realized according to an injection molding process and are, for example, molded at a location other than the location of the installation for manufacture of the receptacles.

As is more apparent in the detailed view, a preform 12 generally has a body 14 which is overall of tubular shape, of cylindrical cross section in a horizontal plane of section, where the body 14 extends vertically along a principal axis A1, here in what may be called the "neck downward" position.

The preform 12 is closed at its upper end by an approximately hemispherical base 16, which corresponds to the upper portion of the body of the preform, this portion being intended to form the base of the receptacle.

Conversely, the preform 12 is open at its lower end, which is shaped to give a neck 18 which already has the definitive shape of the neck or bottleneck of the receptacle.

The preform 12 comprises, at the junction of the body 14 with the neck 18, a collar 20 which extends radially outward, projecting beyond the body 14 and the neck 18.

The neck 18 delimits an annular aperture 22 centered on the axis A1, and the external surface of the neck comprises a thread 24 intended to permit subsequent placement of means of closure of the receptacle, for example a cap (not shown).

The main portions of the preform 12 that are considered in the context of sterilization are respectively the surface of the internal wall 26 and the external surface 28 of the body 14 extending vertically from the base 16 to the collar 20 of the neck 18.

Figure 2:
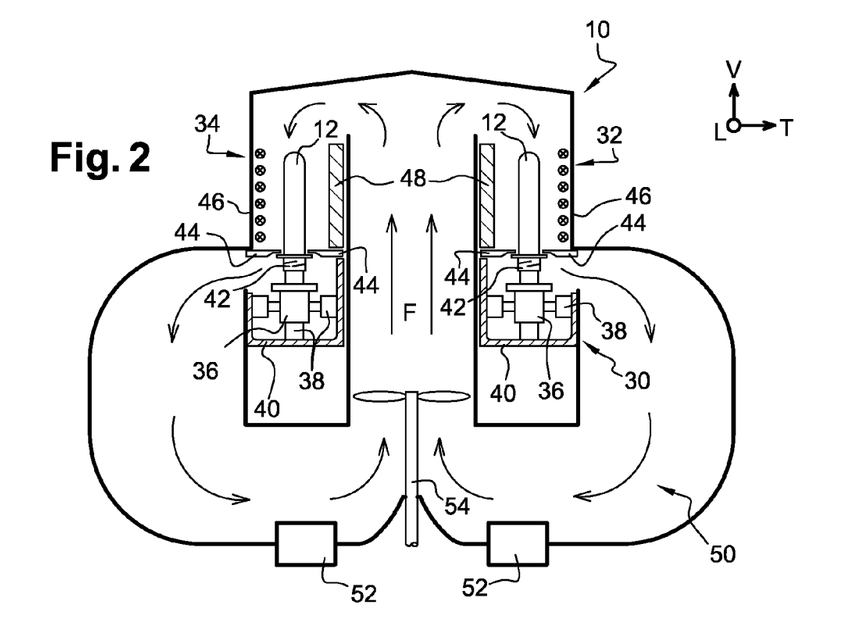
FIG. 2 is a diagrammatic sectional view of the oven of FIG. 1 according to section 2-2, showing the first and third zones of the oven for the infrared heating and the sterilization of the preforms.

As shown in FIG. 2, the oven 10 comprises a device for transport 30 intended to convey successively the preforms 12 in the upstream-to-downstream direction, and equipped with means ensuring that each preform is rotated around its own vertical axis A1.

The preforms 12 are therefore translated from the entry to the oven 10 to the exit, following the direction of the arrows "d" shown in FIG. 1, and pass in the upstream-to-downstream direction through the various zones comprised by the oven 10, at a translational velocity V, while each simultaneously turns around its own axis at a defined velocity of rotation.

The oven 10 comprises successively, in the known manner, a first zone A, which may be called a deep-heating zone, a second zone B, which is an intermediate zone and may be called a residence zone, and a third zone C, which is a heating zone and may be called a final heating zone, these being respectively indicated by a broken line in FIG. 1.

The first zone A for deep heating comprises first means of heating 32 emitting infrared radiation IR1 which is intended to preheat the body 14 of each preform 12 up to a first setpoint temperature TC1.

The first setpoint temperature TC1 corresponding here to the temperature of preheating is preferably between 50° C. and 80° C., for example 70° C.

The second zone B, which is an intermediate residence zone, is interposed in the path of the preforms 12 between the first zone A, which is a heating zone, and the third zone C, which is a heating zone.

Each preform 12 passes through the second zone B in a defined period Δt, which is particularly a function of the translational velocity V of the preforms 12 conveyed by the device for transport 30.

As a function of the applications, the period Δt is, for example, between 2 and 15 seconds, in accordance with the timing of the machine, generally of the order of 5 seconds.

The residence time implemented in the second zone B, between the first and the third zones, which are heating zones, is intended to permit homogeneous distribution within the entire body 14 of the heat transferred by the first means of heating 32.

The third zone C, which is a distributed-heating zone, comprises second means of heating 34 emitting infrared radiation IR2 which is intended to heat the body 14 of each preform 12 up to a second setpoint temperature TC2.

The second setpoint temperature TC2 corresponding here to the temperature of heating is preferably between 80° C. and 130° C., generally of the order of from 90° C. to 110° C.

The heating temperature is particularly defined as a function of the characteristics of the preform 12, for example the material, the thickness of the body 14, etc., and of the receptacle.

The first means of heating 32 and/or the second means of heating 34 are constituted, for example, by infrared radiation lamps, generally in the shape of a tube, which in functioning position in heating zones A and C extend longitudinally and are installed in vertical succession in racks (not shown).

As can be seen in FIG. 2, the device for transport 30 of the preforms 12 comprises means of support 36 on which the preforms 12 are installed in the "neck downward" position, or with the base 16 directed upward, and which are provided with means of guiding 38, for example comprising rollers, inserted into complementary U-shaped rolling tracks 40.

The means of support 36 of the device for transport 30 preferably comprise means for grasping 42 the neck 18 of each preform 12, where the means for grasping 42 advantageously comprise an internal core (not shown) which extends vertically upward in such a way as to penetrate axially along the axis A1 into the interior of the aperture 22 delimited by the neck 18.

The oven 10 comprises means of protection 44, for example in the form of a barrier, forming protective regions intended to ensure thermal protection of the neck 18 of each preform 12 with respect to infrared radiation.

The reason for this is that the neck 18 of each preform 12 has the definitive shape of the neck or bottleneck of the final receptacle, and this must be protected from exposure to the infrared radiation from the means of heating 32, 34 of the oven, in order to avoid any risk of deformation which can more particularly subsequently impair the operation of capping of the receptacle, after filling.

The means of protection 44 extend horizontally above the supports 36, delimiting between them a passage calibrated in such a way as to permit, respectively, heating of the body 14 of the preform 12 extending vertically upward, and, in contrast, protection of the neck 18 extending downward.

The means of protection 44 are advantageously cooled by associated means of cooling (not shown).

The first and third zones A and C of the oven 10, which are heating zones, extend vertically above the means of protection 44 of the necks 18 and comprise, respectively, an external wall 46 and an internal wall 48 between which the bodies 14 of the preforms 12 to be heated proceed, transported by the device 30.

In each of the heating zones A and C of the oven 10, the exterior wall 46 preferably comprises insulating panels associated with the infrared heating lamps 32 or 34, which are vertically superposed, while the opposite interior wall 48 is constituted of reflective panels which can reflect the infrared radiation emitted by the lamps 32, 34 in the direction of the preforms.

The transversal position of each heating lamp 32, 34 can preferably be regulated selectively in the transversal direction, particularly in the third zone C, which is a heating zone, in order to establish a defined heater profile by varying the distance between each of the lamps of the second means of heating 34 and the body 14 and the base 16 of the preforms 12 in the opposite position.

The oven 10 advantageously comprises a device 50 for cooling, which may be called surface cooling, of the body 14 of the preforms 12, this cooling being obtained by circulation of a flow of air F around the preforms, as illustrated by the arrows in FIG. 2.

The device 50 for circulation of air for cooling advantageously comprises means of filtration 52 intended to filter the flow of air for cooling circulated in the oven 10 in such a way as to purify the air and avoid any contamination of the preforms by microorganisms, etc.

The air for cooling circulated in the oven 10 is advantageously constituted by sterile air or air with a high degree of decontamination.

The device 50 preferably comprises means of controlling temperature (not shown) for the temperature of the air.

The oven 10 is equipped with ventilation apertures to permit the passage of the flow of air F blown by means which comprise a rotor 54 and which are intended to promote homogeneous heating within the entire thickness of the preform 12, particularly without excessive heating of the surface layer of material on the external surface 28 of the body 14 and of the base 16.

The reason for this is that the air makes it possible to remove the convected heat generated by the means of heating 32, 34, and to promote the penetration of the infrared radiation IR1, IR2 within the thickness of the material constituting the preform 12.

Figure 5:
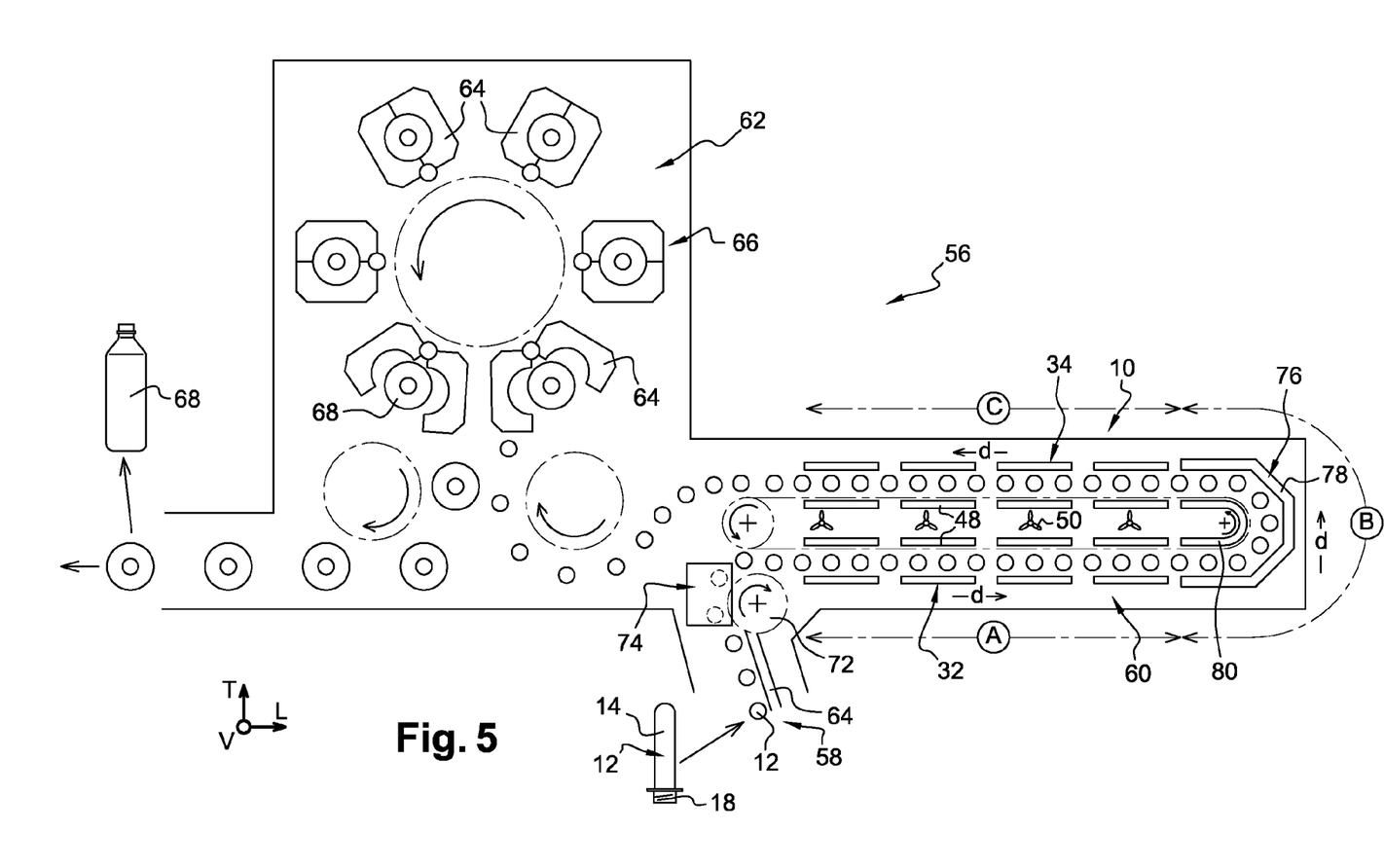
FIG. 5 is a plan view of an installation for manufacture of sterile receptacles comprising an oven according to the invention provided with means of sterilization by ultraviolet radiation for the decontamination of the external surface of the neck and of the body of the preforms and, upstream of the oven, a unit for sterilization for simultaneous achievement, in the oven, of the decontamination of the internal wall of the preform.

FIG. 5 is a diagram of an installation 56 for the manufacture of sterile receptacles, such as bottles, starting from thermoplastic preforms 12 of the type shown in FIG. 1.

An installation 56 of this type principally comprises, in the upstream-to-downstream direction of translation of the preforms 12, a feed device 58, a unit for heat-conditioning 60 comprising at least one oven 10 and its device for transport 30, and a unit for molding 62.

The oven 10 of the unit 60 is intended in the known manner to heat the body 14 of each preform with the aim of permitting molding of the same in the unit for molding 62 situated downstream.

The means of heating 32 and 34 of the oven 10 therefore provide a first function consisting of heating the preforms 12 to soften the same, in accordance with a defined heater profile, by bringing them to a temperature for molding Tm which is a function of the material constituting the preform.

In the case of a preform made from polyethylene terephthalate or PET, the temperature for molding Tm is about 100° C.

The second setpoint temperature TC2 of the second means of heating 34 is equal to the temperature for molding Tm, which is higher than the glass transition temperature Tg of the material constituting the preform 12.

The unit for molding 62 comprises at least one mold 64 and one associated device for blowing 66, in order to convert the preform 12 to a hollow-bodied receptacle 68, which here is a bottle such as that illustrated in detail in FIG. 5, on exit from the unit 62 of the installation 56.

The installation 56 advantageously comprises, downstream of the unit for molding 62 which uses blow molding to convert each preform 12 to a bottle 68, a unit for filling and a unit for capping (not shown).

The feed device 58 is arranged at the entry to the installation 56 and is intended for continuous feed of preforms 12.

A feed device 58 of this type comprises, for example, a hopper (not shown) into which a large number of preforms 12 are tipped, these being withdrawn one by one at the bottom of the hopper in order to be forwarded in succession in the "neck upward" position.

The preforms 12 in this "neck upward" position are preferably forwarded by gravity by means of an inclined slide 70, where the slide is formed by two parallel rails at a distance from one another in such a way as to permit vertical passage of the body 14 of the preforms 12, while each preform 12 is supported by means of its collar 20 on these rails.

Means of grasping capable of grabbing each preform 12 individually are, for example, disposed at the end of the slide 70 and constituted by a loading wheel 72.

The loading wheel 72 is intended to deliver the preforms 12 to the entry to the oven 10 for heat-conditioning, where they are picked up by the device for transport 30.

The preforms 12 are advantageously conveyed through the oven 10 by the device for transport 30 in an opposite "neck downward" position, and means (not shown) are provided for inversion of the preforms between the wheel 72 and the supports 36 comprising an internal core in the device 30.

As explained above, in order to obtain sterile receptacles 68 it is necessary to subject the preform 12 to a total decontamination process.

The installation 56 therefore advantageously comprises a unit for sterilization 74 which is, for example, disposed above the loading wheel 72, upstream of the means for inversion of the preforms 12 and of the entry to the oven 10.

The unit for sterilization 74 (not shown in detail) preferably comprises a device for projection of sterilizing product provided with at least one nozzle capable of projecting, in the form of a vapor jet, a flow of sterilizing product toward the aperture 22 of the neck 18 of each preform 12, the temperature T0 of which is lower than the temperature of condensation Tc of the sterilizing product.

By virtue of the projection unit 74, an approximately uniform condensation film of sterilizing product, intended to sterilize the internal wall 26, is deposited by condensation on at least the internal wall 26 of the preform.

The sterilizing product is advantageously constituted of a compound containing hydrogen peroxide $H_2O_2$ or vaporized hydrogen peroxide $H_2O_2$.

The temperature of activation Ta of the hydrogen peroxide $H_2O_2$ is about seventy degrees Celsius (70° C.).

The sterilizing product $H_2O_2$ is consequently activated from entry of the preform 12 into the first zone A, which is a preheating zone, of the oven 10, and the internal wall 26 of the preform 12 is therefore sterilized.

The reason for this is that the first means for infrared heating 32 of the oven 10 are intended to heat the body 14 of the preform 12 up to the first setpoint temperature TC1, which is advantageously higher than or equal to the temperature of activation Ta.

Furthermore, the second means of infrared heating 34 of the third zone C, which is a heating zone, of the oven 10 are intended to heat the preform 12 to the second setpoint temperature TC2 equal to the temperature for molding Tm (from 90 to 130° C.) which is above the temperature of evaporation Te of a sterilizing product, for example $H_2O_2$.

The sterilizing product ($H_2O_2$) is consequently automatically eliminated by evaporation during the heating in the zone C, and the final receptacle 68 obtained therefore has at most a few minute traces of sterilizing product conforming with the requirements of applicable legislation.

The means for heating 32 and 34 of the oven 10 therefore advantageously provide not only a first conventional function for heating with an aim of molding, but also a second function consisting in thermal activation of the sterilizing product by heating in such a way that at least the internal wall 26 of the preform 12 is sterilized and then that said product previously activated is removed by evaporation in order that almost every trace thereof is removed from the final receptacle 68.

The internal wall 26 of the preform 12 is advantageously in contact with the condensation film of sterilizing product deposited by condensation and activated from entry into the oven 10 during a time which may be called internal decontamination and which corresponds at least to the period that a preform takes to pass successively through the first zone A.

As a function of the temperature, the decontamination of the internal wall 26 can continue in all or a portion of the second zone B, which is an intermediate zone, prior to progressive evaporation of the film of sterilizing product in the third zone C.

Once the sterilization of the internal wall 26 of the preform 12 has been advantageously achieved by a chemical route in the manner described above, it is then necessary to proceed to the sterilization of the external surface 28 of the preform 12, in order to manufacture sterile receptacles having a high degree of decontamination.

The reason for this is that, as has been explained above, the additional sterilization of the external surface 28 of the body 14 of the preform 12, and preferably of the neck 18, is the only method that can reduce or remove the risks of cross-contamination according to which microorganisms, bacteria, or spores, etc. present on the exterior of the preform can in particular be reintroduced into the interior of the preform 12, particularly by the air circulating in the unit for molding 62 during the blow molding operation.

In accordance with the invention, the oven 10 is characterized in that it comprises the first means for heating 32, the means for sterilization 76 which are arranged in the second zone B, which is an intermediate residence zone, and which are capable of emitting ultraviolet (UV) radiation, and the second means for heating 34, in such a way that at least the external surface 28 of the body 14 of the preform 12 is sterilized up to the defined degree of decontamination.

The process for sterilization implemented in an oven 10 according to the invention is advantageously capable of sterilizing at least the external surface 28 of the body 14 of the preform 12 up to a defined degree of decontamination.

The reason for this is that the process for sterilization implemented in an oven 10 according to the invention comprises at least the following successive steps:
  a first step for decontamination by heating, in the course of which the body 14 of the preform 12 is preheated by the first means for heating 32 up to the first setpoint temperature TC1;
  a second step for decontamination by ultraviolet (UV) radiation, during the course of which at least the external surface 28 of the body 14 of the preform 12 is exposed for a defined period Δt to ultraviolet (UV) radiation emitted by means of sterilization 76; and
  a third step for sterilization by heating, during the course of which the body 14 of the preform 12 is heated by the second means of heating 34 up to a second setpoint temperature TC2.

A process for this type for sterilization is therefore advantageously capable of being implemented in an oven 10 such as the oven 10 of a unit for heat-conditioning 60 of an installation 56 for manufacture of sterile receptacles starting from thermoplastic preforms 12 intended for conversion by blow molding or by stretch blow molding.

In an oven 10 according to the invention, sterilization of at least the external surface 28 of the body 14 of the preform 12 is obtained by three steps comprising successively:
  heating or preheating of the body 14 of the preform 12 up to the first setpoint temperature TC1 corresponding to a first given temperature for decontamination;
  irradiation of at least the body 14 of the preform 12 by ultraviolet (UV) radiation during a defined period; and
  heating of the body 14 of the preform 12 up to the second setpoint temperature TC2 corresponding to a second given temperature for decontamination.

The ultraviolet (UV) radiation emitted by the means of sterilization 76 in the second zone B, which is an intermediate residence zone, advantageously sterilizes the air in the flow of air for cooling circulating around the preforms 12.

Figure 3:
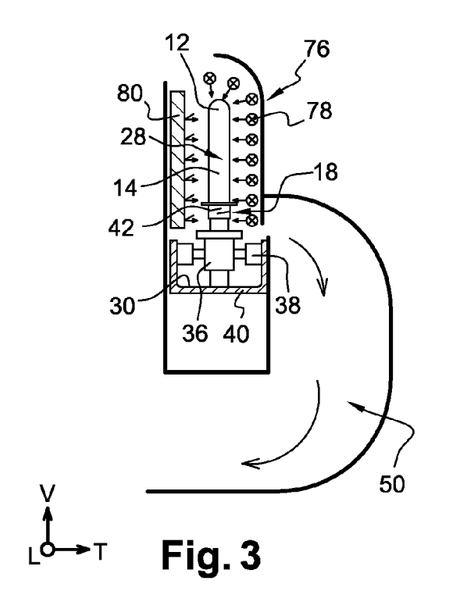
FIG. 3 is a diagrammatic sectional view of the oven of FIG. 1 in the second zone, which is a residence zone, according to section 3-3, and shows an example of placing of the means of sterilization by ultraviolet radiation comprising associated reflectors.

According to one embodiment shown in FIG. 3, the oven 10 comprises, in the second zone B, which is an intermediate residence zone, means for sterilization 76 by ultraviolet (UV) radiation constituting lamps 78 providing ultraviolet (UV) radiation and associated means for reflection 80, for example reflectors.

The reflectors 80 are advantageously arranged in the interior of the oven 10 opposite to the lamps 78 providing ultraviolet (UV) radiation, in such a way as to reflect selectively the ultraviolet (UV) radiation emitted in the direction of the preforms 12.

The overall arrangement here of the means for sterilization 76 by ultraviolet radiation generated by the lamps 78 providing ultraviolet (UV) radiation and by the means for reflection 80 is that of a "horseshoe" along the path of the preforms 12 in the second zone B and on either side of the latter which are proceeding at the velocity V, while rotating around their own axes, between the UV lamps 78 and the reflectors 80.

Figure 4:
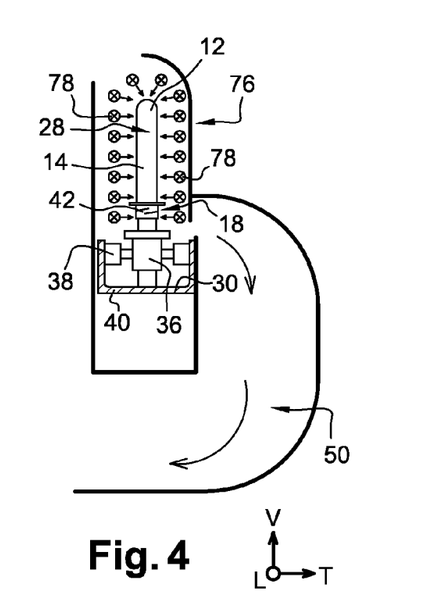
FIG. 4 is a view analogous to FIG. 3, which illustrates one embodiment according to which the means for sterilization by ultraviolet radiation are arranged on either side of the preforms.

According to one embodiment shown in FIG. 4, the reflectors 80 arranged in the interior are replaced by a wall provided with ultraviolet (UV) lamps 78, in such a way that the second zone B, which is an intermediate residence zone, of the oven 10 comprises supplementary means for emission of ultraviolet (UV) radiation in order to sterilize the preforms 12.

This type of embodiment advantageously permits an overall increase in the amount of ultraviolet (UV) radiation emitted, and thus in the amount of radiation received by the external surface 28 of the body 14 and by the neck 18 of the preform 12, in such a way as to increase the final degree of decontamination for the same velocity V of translation of the preforms 12.

Furthermore, according to this embodiment, the means for sterilization 76 permit maintenance of a high degree of decontamination even when the period Δt decreases at a higher velocity V.

The reason for this is that the period Δt corresponds to the period of exposure of the external surface 28 of the body 14 and of the neck 18 of the preform 12 to the ultraviolet (UV) radiation.

The average temperature in the second zone B, which is a residence zone, is of the order of from 40 to 50° C., and the means for protection 44 of the necks 18 are therefore advantageously removed here.

The means for sterilization 76, for example the lamps 78 and/or the reflectors 80, are advantageously disposed in such a way that the neck 18 is also irradiated by ultraviolet (UV) radiation.

The lamps 78 of the means for sterilization 76 are constituted by lamps of standard type, for example in the form of a tube, which function reliably, with normal lifetime, at an ambient temperature of the order of 50° C. in the second zone B, which is an intermediate zone.

The device for transport 30 advantageously comprises means for grasping 42 the neck 18 of each preform 12, these means being equipped with the internal core penetrating axially into the interior of the aperture 22 of the neck 18 of the preform 12, in such a way that the external surface of the neck 18 of the preform 12 is entirely irradiated by the ultraviolet (UV) radiation emitted by the means for sterilization 76.

The degree of decontamination of the external surface of the neck 18 of the preform 12 is therefore at least equal to 2.5 log.

In order to determine the final degree of decontamination, tests were carried out with preforms 12 contaminated by spores of the bacillus "Atrophaeus 9372" used here as a referent, giving the results detailed below.

The reason for this is that the spores of this bacillus are nowadays considered to be a worldwide referent for determination of the level of sterility or asepsis, not only by institutions (FDA, etc.) but also by industry, more particularly in a sector such as agrofood.

If the only process carried out is a heat-sterilization step on the external surface 28 of the body 14 of the preform 12, by heating with infrared radiation in an oven 10, the degree of decontamination obtained is relatively slight, generally below 0.5 log.

Equally, if the only process carried out is an operation for sterilization of the external surface 28 of the body 14 of the preform 12 by irradiation with ultraviolet (UV) radiation during a defined period, the degree of decontamination obtained is then between 2 log and 3 log, for example of the order of 2.5 log.

The period of irradiation of the preforms 12 by ultraviolet (UV) radiation advantageously corresponds to the defined period Δt taken by each preform 12 to pass through the second zone B, which is a residence zone, of a given oven, where each preform 12 is conveyed through the oven 10 by the device for transport 30 at a defined translational velocity V which is a function of the type of oven and of the applications.

By way of comparison, the tests carried out demonstrated that when a process carries out consecutively a step for sterilization by ultraviolet (UV) radiation and then a step for heat-sterilization by infrared, or conversely a step for heat-sterilization by infrared and then a step for sterilization by ultraviolet (UV) radiation, the overall degree of decontamination obtained remained similar to that obtained previously with the single step for sterilization by ultraviolet (UV) radiation, i.e. of the order of 2.5 log.

The results obtained therefore demonstrate clearly that a single step for sterilization by heating, particularly by infrared, cannot increase the degree of decontamination beyond the degree obtained only by sterilization by ultraviolet (UV) radiation.

Surprisingly, however, the combination of the three successive steps implemented in an oven 10 according to the invention obtains a degree of decontamination which is both unexpected and particularly high.

By way of comparison, a final degree of decontamination of the order of 5 log to 6 log was obtained during these tests, or a level of sterilization of the external surface 28 of the body 14 of the preform 12 which is more than twice as high as that obtained previously by a process carrying out consecutively only two steps for sterilization by infrared heating and by irradiation by ultraviolet (UV) radiation or vice versa.

The implementation of the process in an oven 10 according to the invention comprising means for sterilization 76 is carried out at least in accordance with the successive steps for decontamination described above in order to sterilize at least the external wall 28 of the body 14 of the preform 12.

The means for heating 32 and 34 of the oven 10 consequently also provide a third function consisting in promoting the decontamination of the preform 12 by combining the sterilizing effects of infrared heating and of irradiation by ultraviolet (UV) radiation, in order to obtain a particularly high final degree of decontamination.

The final degree of decontamination of the external surface 28 of the body 14 is advantageously obtained solely by the combination of these three steps for sterilization which, carried out consecutively, will permit successive removal of at least a major portion of the microorganisms, bacteria, or spores, etc. present on the external surface 28 of the body 14 of the preform 12, these being destroyed and/or impaired by the heat from the infrared radiation IR1, and then, at the very least in weakened condition, have increased vulnerability by virtue of which the ultraviolet (UV) radiation will destroy or impair other, additional microorganisms, etc., and the majority of the microorganisms etc. remaining on the external surface 28 of the body 14 of the preform 12 are then destroyed by the powerful heat of the infrared radiation IR2.

More specifically, because certain microorganisms, bacteria, or spores, etc. are present on the external surface 28 of the body 14 of the preform 12 at the exit from the second zone B and have not by this stage been impaired, it is not possible to guarantee that the degree of decontamination is irreversible; irreversible destruction of these organisms is not obtained until after passage through the third zone C for exposure to infrared radiation IR2.

The process for sterilization advantageously comprises a preliminary step for sterilization of the internal wall 26 of the preform 12 which precedes the first step for preheating and consists in projecting, in the form of a vapor jet, a flow of sterilizing product toward the aperture 22 of the neck 18 of each preform 12, the temperature T0 of which is lower than the temperature of condensation Tc of the sterilizing product, in such a way as to deposit by condensation on the internal wall 26 of the preform 12 an approximately uniform condensation film of sterilizing product.

The uniform condensation film of condensed sterilizing product, which is then thermally activated by the first means for heating 32 of the oven, and is then removed by evaporation by the second means for heating 34, permits sterilization of the internal wall 26 with a degree of decontamination of at least 3 log.

By virtue of the invention, it is possible, starting from preforms 12 which are sterilized and heat-conditioned in an oven 10 according to the invention, to manufacture sterile receptacles having a particularly high final degree of decontamination, not only on the internal wall 26 of the preform 12 but also on the external surface 28 of the body 14 of the preform 12.

The reason for this is that the second function of the means for heating 32 and 34 of the oven 10 is thermal activation and then removal by evaporation of the sterilizing product deposited by condensation.

The first temperature for preheating TC1 is therefore advantageously higher than or equal to the temperature of activation Ta of the sterilizing product, in such a way that the internal wall 26 of the preform 12 is sterilized, while the second temperature for heating TC2 is advantageously higher than the temperature of evaporation Te of the sterilizing product, in such a way that the sterilizing product previously thermally activated is removed by evaporation.

The process for sterilization according to the invention can advantageously be implemented in a manner which is particularly simple, reliable, and cost-effective, particularly in an installation for manufacture of sterile receptacles where the installation is of the type described and shown in FIG. 5.

More specifically, an oven for conditioning 10 conforming with the teaching described above for the invention comprises successively:

the first zone A, which may be called a deep-heating zone, comprising the first means for heating 32 by infrared radiation IR1 intended to preheat the body 14 of each preform 12 up to said first setpoint temperature TC1;

the second zone B, which is an intermediate residence zone, through which zone, which is interposed in the path of the preforms between the first zone A, which is a heating zone, and the third zone C, which is a heating zone, each preform passes, during a defined period t; and the third zone C, which is a distributed-heating zone, comprising the second means for heating 34 by infrared radiation IR2, intended to heat the body 14 of each preform 12, in accordance with a defined heater profile, up to said second setpoint temperature TC2.

The structural modifications to be applied to an existing oven 10 of this type in order to install within it the means for sterilization 76 by ultraviolet (UV) radiation are consequently minimal and exclusively located in the second zone B, which is a residence zone.

The infrared radiation of the first and second means for heating 32, 34 advantageously have a triple action, i.e. heating of the preform 12 with the aim of converting the same by blow molding or by stretch blow molding into a sterile hollow-bodied receptacle, sterilization (or decontamination) of the internal wall 26 by activation and evaporation of the sterilizing product and, in combination with the irradiation by ultraviolet (UV) radiation, sterilization, which may be called thermal sterilization, of the external surface 28 of the body 14.

The invention claimed is:
1. An oven (10) for heat-conditioning of thermoplastic preforms, particularly intended for equipping an installation for manufacture of sterile receptacles, comprising a device for transport (30) of the preforms (12) which are rotated around their own axes and successively conveyed within at least:
- one first zone A, which may be called a deep-heating zone, comprising first means for heating (32) by infrared radiation (IR1) intended to preheat the body (14) of each preform (12) up to a first setpoint temperature (TC1);
- a second zone B, which is an intermediate zone, and which may be called a residence zone, through which zone, which is interposed in the path of the preforms (12) between the first zone A, which is a heating zone, and a third zone C, which is a heating zone, each preform (12) passes, during a defined period (t);
- the third zone C, which may be called a distributed-heating zone, comprising second means for heating (34) by infrared radiation (IR2), intended to heat the body (14) of each preform (12), in accordance with a defined heater profile, up to a second setpoint temperature (TC2),
- characterized in that the oven (10) comprises means for sterilization (76, 78, 80) by emission of ultraviolet (UV) radiation, arranged in the second zone B, which is an intermediate residence zone, in such a way as to sterilize at least the external surface (28) of the body (14) of the preform (12) up to a defined degree of decontamination.

2. The oven as claimed in claim 1, characterized in that the oven (10) comprises means for reflection (80), such as reflectors, arranged in the second zone B, which is an intermediate residence zone, opposite to the means for sterilization (76) by ultraviolet (UV) radiation, such as lamps (78), in such a way as to reflect selectively the ultraviolet (UV) radiation emitted in the direction of the preforms (12) passing between the means for sterilization (UV) and the means for reflection (80).

3. The oven according to claim 1, comprising a device for the cooling (50) of the preforms (12) by passage of a current of air (F) around the preforms (12), characterized in that the ultraviolet (UV) radiation emitted by the means for sterilization (76) in the second zone B, which is an intermediate residence zone, sterilizes the air circulating around the preforms (12).

4. The oven as claimed in claim 1, characterized in that the device for transport (30) comprises means for grasping (42) the neck (18) of each preform (12) comprising at least one internal core which penetrates axially into the interior of the neck (18) of the preform (12) in such a way that the ultraviolet (UV) radiation emitted by the means for sterilization (76) irradiates entirely the neck (18) of the preform (12).

5. An installation (56) for the manufacture of sterile receptacles (68) starting from a decontaminated thermoplastic preform (12), comprising at least:
- one device for feed (58) of preforms;
- one unit for heat-conditioning (60) comprising a device for transport (30) of preforms through at least one oven (10) intended to heat each preform (12) with the aim of molding of the same; and
- a unit for molding (62) intended to convert each preform (12) to a hollow-bodied receptacle (68),
- characterized in that the oven (10) for heat-conditioning comprises:
  - first means for heating (32) intended to decontaminate at least the external surface (28) of the body (14) of the preform (12) by preheating the body (14) of each preform (12) up to a first setpoint temperature (TC1);
  - means for sterilization (76) by emission of ultraviolet (UV) radiation intended to decontaminate at least the external surface (28) of the body (14) of the preform (12) by irradiation of the preform (12) exposed during a defined period (Δt) to ultraviolet (UV) radiation emitted by the means for sterilization (76); and
  - second means for heating (34) intended to decontaminate at least the external surface (28) of the body (14) of the preform (12) by heating the body (14) of each preform (12) up to a second setpoint temperature (TC2),
  - in such a way as to sterilize at least the external surface (28) of the body (14) of the preform (12) up to a defined degree of decontamination.

6. The installation (56) as claimed in claim 5, characterized in that it comprises, upstream of the oven (10) for heat-conditioning, a unit for sterilization (74) comprising a device for projection of sterilizing product provided with at least one nozzle capable of projecting, in the form of a vapor jet, a flow of sterilizing product toward the aperture (22) of the neck (18) of each preform (12), the temperature (T0) of which is lower than the temperature of condensation (Tc) of the sterilizing product, in such a way as to deposit by condensation on at least the internal wall (26) of the preform (12) an approximately uniform condensation film of sterilizing product, intended to sterilize at least the internal wall (26).

7. The installation (56) as claimed in claim 6, characterized in that the first temperature of preheating (TC1) and/or the second temperature of heating (TC2) of the body (14) of the preform (12) in the oven (10) are higher than or equal to the temperature of activation (Ta) of the sterilizing product, in such a way as to sterilize the internal wall (26) of the preform (12) by activation of the sterilizing product by heating.

8. The installation (56) as claimed in claim 7, characterized in that the first temperature of preheating (TC1) and/or the second temperature of heating (TC2) of the body of the preform (12) in the oven (10) are higher than the temperature of evaporation (Te) of the sterilizing product, in such a way as to remove by evaporation the sterilizing product activated by heating.

9. The oven according to claim 2, comprising a device for the cooling (50) of the preforms (12) by passage of a current of air (F) around the preforms (12), characterized in that the ultraviolet (UV) radiation emitted by the means for sterilization (76) in the second zone B, which is an intermediate residence zone, sterilizes the air circulating around the preforms (12).

10. The oven as claimed in claim 2, characterized in that the device for transport (30) comprises means for grasping (42) the neck (18) of each preform (12) comprising at least one internal core which penetrates axially into the interior of the neck (18) of the preform (12) in such a way that the ultraviolet (UV) radiation emitted by the means for sterilization (76) irradiates entirely the neck (18) of the preform (12).

11. The oven as claimed in claim 3, characterized in that the device for transport (30) comprises means for grasping (42) the neck (18) of each preform (12) comprising at least one internal core which penetrates axially into the interior of the neck (18) of the preform (12) in such a way that the ultraviolet (UV) radiation emitted by the means for sterilization (76) irradiates entirely the neck (18) of the preform (12).

12. The oven as claimed in claim 9, characterized in that the device for transport (30) comprises means for grasping (42) the neck (18) of each preform (12) comprising at least one internal core which penetrates axially into the interior of the neck (18) of the preform (12) in such a way that the ultraviolet (UV) radiation emitted by the means for sterilization (76) irradiates entirely the neck (18) of the preform (12).

* * * * *